United States Patent [19]

Schirmann et al.

[11] 4,049,712
[45] * Sept. 20, 1977

[54] METHOD FOR MANUFACTURING HYDRAZODICARBONAMIDE

[75] Inventors: Jean-Pierre Schirmann, Brignais; Francis Weiss, Pierre-Benite, both of France

[73] Assignee: Produits Chimiques Ugine Kuhlmann, Paris, France

[*] Notice: The portion of the term of this patent subsequent to Aug. 3, 1993, has been disclaimed.

[21] Appl. No.: 265,749

[22] Filed: June 23, 1972

[30] Foreign Application Priority Data

June 25, 1971 France ............................ 71.23198

[51] Int. Cl.$^2$ .................... C07C 133/02; C01B 21/16
[52] U.S. Cl. .................... 260/554; 260/239 AA; 260/566 B; 423/407
[58] Field of Search ............................ 260/554, 566 B; 423/407

[56] References Cited

U.S. PATENT DOCUMENTS

| | | | |
|---|---|---|---|
| 2,692,281 | 10/1954 | Newby et al. | 260/554 |
| 2,801,195 | 7/1957 | Doerr | 148/23 |
| 3,227,753 | 1/1966 | Mehr et al. | 260/554 |
| 3,415,882 | 12/1968 | Jenkins et al. | 260/566 B |
| 3,527,753 | 9/1970 | Needham et al. | 260/566 B |

FOREIGN PATENT DOCUMENTS 1,186,021 4/1970 United Kingdom

OTHER PUBLICATIONS

Curtius et al., Journal F. Prakt. Chemie, Band 44, No. 2, pp. 199–200, (1891).

*Primary Examiner*—James O. Thomas, Jr.
*Assistant Examiner*—G. T. Breitenstein
*Attorney, Agent, or Firm*—Pennie & Edmonds

[57] ABSTRACT

This invention relates to a method for preparing hydrazodicarbonamide

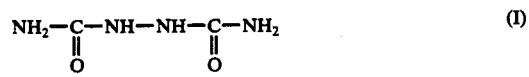

which comprises reacting urea, sulfuric acid, water and an azine or a solution containing an azine of the formula

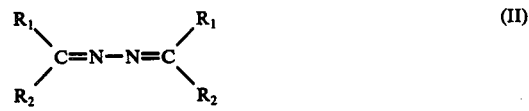

wherein $R_1$ is hydrogen and $R_2$ or $R_1$ and $R_2$ each is a straight or branched alkyl radical or cycloalkyl radical of up to 6 carbon atoms or $R_1$ and $R_2$ of both the $>C=N-$ moieties together form a straight or branched chain alkylene radical of from 3 to 5 carbon atoms and recovering the hydrazodicarbonamide from the reaction medium.

5 Claims, No Drawings

METHOD FOR MANUFACTURING HYDRAZODICARBONAMIDE

BACKGROUND OF THE INVENTION

I. Field of the Invention

This invention relates to methods for preparing the compound hydrazodicarbonamide which has the formula

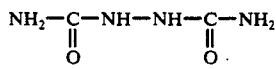

II. Description of the Prior Art

Hydrazodicarbonamide can be obtained by the known method of reacting urea and hydrazine sulfate in an acid medium (see for example, Kirk-Othermer Encyclopedia of Chemical Technology, 2nd Edition, Vol. II).

Hydrazodicarbonamide can also be obtained by reacting a 3,3-dialkyldiazacyclopropane with urea in the presence of sulfuric acid (Japanese patent application No. Sho-42-76931)

One method for preparing azines comprises the oxidation of ammonia in the presence of a ketone or aldehyde by means of an oxidizing medium comprising hydrogen peroxide and cyanogen or a nitrile. This method solely invented by the instant inventors is fully disclosed in commonly assigned pending U.S. patent application Ser. No. 152,413, filed June 11, 1971, now abandoned, which is incorporated by reference herein.

Another method for preparing azines comprises oxidizing a secondary alcohol in the liquid phase to form peroxide products of the auto-oxidation of the alcohol and subsequently reacting the peroxide products with ammonia in the presence of cyanogen or a nitrile. This method is fully disclosed in commonly assigned pending U.S. patent application Ser. No. 230,038, filed Feb. 28, 1972, now abandoned, which is also incorporated by reference herein.

The azines formed by each of these methods can be recovered employing various methods such as decantation, liquid-liquid extraction, distillation, and so forth. The azines can be utilized herein in either the substantially pure state or in aqueous or organic solution. If solutions of azines are used, they can also contain unreacted products from which the azines are derived, as for example, ketone or aldehyde in the event the method of Ser. No. 152,413, now abandoned, is employed.

The azines which are useful in the method of this invention can be prepared by any other known method, for example, by oxidizing $NH_3$ with chlorine in the presence of a ketone as disclosed in U.S. Pat. No. 3,527,753 or by the addition of acetone to a solution of hydrazine according to the Raschig process.

SUMMARY OF THE INVENTION

It has been surprisingly discovered that hydrazodicarbonamide can be simply and economically manufactured in high yield by the method of this invention which comprises reacting urea, sulfuric acid and an azine or a solution containing an azine of the formula

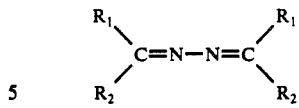

wherein $R_1$ is hydrogen and $R_2$ or $R_1$ and $R_2$ each is a straight or branched alkyl radical or cycloalkyl radical of up to 6 carbon atoms or $R_1$ and $R_2$ of both the $>C=N—$ moieties together form a straight or branched chain alkylene radical of from 3 to 5 carbon atoms and recovering the hydrazodicarbonamide from the reaction medium.

The reaction of azine, urea, sulfuric acid and water can be illustrated as follows:

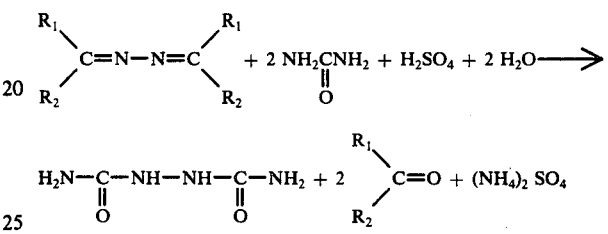

DESCRIPTION OF THE PREFERRED EMBODIMENTS

The method of this invention employs azines which can be prepared by either of the methods disclosed in Ser. No. 152,413, filed June 11, 1971, now abandoned, or Ser. No. 230,038 filed Feb. 28, 1972, now abandoned.

In the method of Ser. No. 152,413, now abandoned, a carbonyl compound

is reacted with cyanogen or a nitrile of the formula

to form the azine (II).

In the formula (III) carbonyl compound $R_1$ is hydrogen and $R_2$ or $R_1$ and $R_2$ each is a straight or branched alkyl radical or cycloalkyl radical of up to 6 carbon atoms or $R_1$ and $R_2$ together form a straight or branched chain alkylene radical of from 3 to 5 carbon atoms.

In the formula (IV) nitrile, $R_3$ is an unsubstituted or substituted saturates aliphatic, acyclic or cyclic radical of from 1 to 12 carbon atoms or a benzenyl or pyridinyl radical and $n$ is an integer from 1 to 6.

When $R_1$ of the carbonyl compound (III) is hydrogen, the carbonyl compound is an aldehyde and the resulting azine (II) is an aldazine (V). When $R_1$ of the carbonyl compound (III) is other than hydrogen, the carbonyl compound is a ketone and the resulting azine (II) is a ketazine (VI). Reacting either an aldazine or ketazine conforming to formula (II) with urea, water and sulfuric acid according to the method of this invention results in the production of hydrazodicarbonamide.

Some examples of ketones conforming to formula (III) which are advantageously employed in the above process include acetone, 2-butanone, 2-pentanone, 3-pentanone, methylisopropylketone, methylisobutylketone, methylcyclohexylketone, acetophenone, benzophenone, cyclobutanone, cyclopentanone, cyclohexanone, 2-methylcyclohexanone, 4-methylcyclohexanone, 2,4-dimethylcyclohexanone, 3,3,5-trimethylcyclohexanone, cycloheptanone, cyclooctanone, cyclodecanone and cyclododecanone.

Some examples of aldehydes of formula (III) which are advantageously employed in the above process include acetaldehyde, propionaldehyde, butyraldehyde, isobutyraldehyde, valeric aldehyde, pivaldehyde, oenathal, hexahydrobenaldehyde, p-nitrobenaldehyde and β-methoxypropionaldehyde.

The nitriles conforming to formula (IV) which can be advantageously employed in the process include the mononitriles and polynitriles wherein the radical $R_3$ is a hydrocarbon radical containing up to 12 carbon atoms, which hydrocarbon radical can be a cyclic or acyclic radical or an aromatic radical such as a benzenyl or pyridinyl radical. Moreover the radical $R_3$ can contain substituents advantageously selected from amongst those groups which are not susceptible to oxidation under the conditions of the reaction, as for example, amide, carboxylic, carboxylic ester, nitro, fluoro, chloro, bromo, iodo, hydroxy, oxyether, acetal, epoxy, sulfoxide, sulfur, sulfone and sulphonic acid groups.

In addition to cyanogen, specific examples of formula (IV) nitriles which are advantageously employed include acetonitrile, propionitrile, butyronitrile, isobutyronitrile, cyclohexylcarboxylic nitrile, benzonitrile, tolunitriles, the cyanopyridines, the mono-di- and trichloroacetonitriles, m-chlorobenzonitrile, p-methoxybenzonitrile, p-nitrobenzonitrile, m-trifluoromethylbenzonitrile, glycolonitrile, epsilon-hydroxycapronitrile, cyanoacetic acid, the amides and alkyl esters of cyanoacetic acid, the amide and alkyl esters of beta-cyanopropionic acid, malononitrile, succinonitrile, glutaronitrile, adiponitrile, pimelonitrile, suberonitrile, the phthalonitriles and the nitriles which are prepared from the cyanoethylation of acrylonitrile or methacrylonitrile with water, an alcohol, a polyol and a carboxylic acid.

Examples of nitriles prepared from cyanoethylation include beta-hydroxyprorionitriles such as β,β'-oxydipropionitrile, β-alkoxyproprionitriles such as β-methoxy-propionitrile, the cyanoethylation products of ethyleneglycol, propyleneglycol, glycerol and sorbitol. Certain of these nitriles can be formed in situ depending upon the constituents of the reaction medium, most notably, water or alcohol, by the reaction of acrylonitrile or methacrylonitrile thus permitting the use of these ethylenic nitriles as starting materials in the process.

An advantageous method for preparing the azines according to Ser. No. 152,413, now abandoned, comprises reacting the components of the reaction medium in an aqueous solution or in the presence of a solvent. The solvent is advantageously selected from among the mono alkanols having from one to four carbon atoms, for example, methanol, ethanol, n-propanol, isopropanol, n-butanol, sec-butanol isobtuanol and tert-butanol. The reaction temperature is advantageously between about 0° and about 100° C. The reaction can be carried out at about atmospheric pressure or at a pressure of up to about 10 atmospheres of pressure if necessary to maintain the ammonia in the reaction medium.

The reactants can be employed in stoichiometric amounts but a molar lack or excess of one or several reagents can also be utilized. For example, from about 0.2 to about 5 moles of aldehyde or ketone and ammonia per mole of hydrogen peroxide can be employed. The quantity of nitrile which is advantageously employed can vary from about 1 to about 10 equivalents of nitrile per mole of hydrogen peroxide.

The reactants can be used in their commercially available form. For example, hydrogen peroxide can be used in aqueous solutions of 30–90% hydrogen peroxide by weight and ammonia can be used either in anhydrous form or in the usual aqueous solution.

The reactants can be introduced into the reactor either simultaneously or in random sequence at a rate which will permit effective control of the exothermic reaction. The carbonyl compounds can be reacted with hydroperoxide in the known manner and the resulting peroxides can then be reacted with ammonia in the presence of nitrile. Similarly, the carbonyl compounds can be reacted with ammonia before adding the hydrogen peroxide and nitrile. And finally, an aminoperoxide can be prepared in the known manner by the reaction of a carbonyl compound, ammonia and hydrogen peroxide and this aminoperoxide can then be reacted with a nitrile to yield an azine.

It is advantageous to add a stabilizing agent for hydrogen peroxide to the reaction medium such as phosphoric acid, nitrilotriacetic acid, ethylenediaminotetraacetic acid, the sodium salts of the aforesaid acids, and as a catalyst, an effective amount of an ammonium salt or an alkaline metal salt, for example, a lithium, sodium or potassium salt of a mineral hydracid or oxyacid, or of an aliphatic or aromatic carboxylic acid or arylsulphonic acid having less than 20 carbon atoms, the anions of which are stable under the oxidizing conditions of the reaction medium.

Some of the useful ammonium salts or alkaline metal salts include the ammonium, lithium, sodium and potassium salts whose anion is a fluoride, chloride, sulphate, nitrate, phosphate, pyrophosphate, borate, carbonate, formate, acetate, proionate, butyrate, isobutyrate, hexanoate, octanoate, dodecanoate, stearate, oxalate, succinate, glutarate, adipate, benzoate, phthalate, methanesulphonate, ethanesulphonate, benzenesulphonate, and p-toluenesuphonate. The quantity of salt used can vary from 0.01 to 2% by weight of the total reaction mixture. The salt can be formed in situ. For example, if it is desired to employ an ammonium salt, the salt may be formed in situ by adding an acid to the ammonia-containing reaction medium.

In the method of Ser. No. 230,038, now abandoned, a secondary alcohol of the formula

(VII)

is reacted with molecular oxygen or a gaseous mixture containing the same, at a temperature and pressure which is sufficient to maintain the alcohol in the liquid phase and result in a liquid phase mixture containing the peroxidic products of the auto-oxidation of the alcohol and reacting the auto-oxidation products with ammonia, cyanogen or the nitrile

(IV)

numerous examples of which are given above, to form a ketazine (VI) conforming to formula (II). In the formula (VII) alcohol, $R_1$ and $R_2$ each is a straight or branched alkyl radical or cycloalkyl radical of up to 6 carbon atoms or $R_1$ and $R_2$ together form a straight or branched chain alkylene radical of from 3 to 5 carbon atoms. Reacting the ketazine with urea, water and sulfuric acid according to the method of this invention results in the production of hydrazodicarbonamide.

Some examples of secondary alcohols conforming to formula (VII) which are advantageous in carrying out this method include isopropanol, 2-butanol, 2-pentanol, 3-pentanol, 3-methyl-2-butanol, 4-methyl-2-pentanol, 2-octanol, 1-cyclohexylethanol, 1-phenylethanol, diphenylcarbinol, cyclobutanol, cyclopentanol, cyclohexanol, 2-methylcyclohexanol, 3-methylcyclohexanol, 3,3,5-trimethylcyclohexanol, cycloheptanol, cyclooctanol and cyclododecanol.

As will be readily understood by one skilled in the art, many other secondary alcohols in addition to those specifically recited herein can be employed. Moreover, the alcohol chosen can contain substituents which are stable in the reaction medium, as for example, methyl, methoxy, chloro, fluoro, or nitro groups.

In addition to producing a ketazine, the method can result in generally small quantities of derivatives of hydrazine and ketone, notably a diaziridine of the formula:

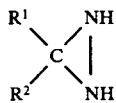
(VIII)

and a hydrazone of the formula

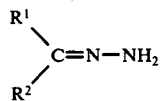
(IX)

For the sake of simplicity, the method of Ser. No. 230,038, now abandoned, is referred to as one for preparing ketazines although it is to be understood that small quantities of the compounds of formulas (VIII) and (IX) can also be produced.

The auto-oxidation of the secondary alcohol or mixture of secondary alcohols can be carried out in known and conventional ways. The alcohol or mixture thereof is contacted with molecular oxygen or with a gas containing oxygen, as for example, air, under such conditions of pressure and temperature that the alcohol as well as the peroxide compounds, ketone and hydrogen peroxide resulting from the auto-oxidation reaction will be in the liquid phase.

The temperature of the reaction can be maintained between about 60° and 180° C and advantageously between about 80° and 160° C. The reaction can be made to take place at atmospheric pressure if the nature of the starting materials and the temperature selected for the reaction permit. This reaction can also be made to take place at a pressure higher than the atmospheric pressure, for example, up to 50 atmospheres, if such pressure is necessary to maintain the reaction products in the liquid phase.

The reaction medium should be kept free of any heavy metal ions which risk catalyzing the decomposition of the peroxidic compounds. It is therefore advantageous to take such precautions to prevent the presence of these ions by the addition of agents to the reaction medium capable of sequestering the ions, for example, an alklaine phosphate and by the use of inert materials for the construction of the oxidation reactor, for example, glass enammelled steel, stainless steel, and so forth.

It is known that the initiation of the oxidation reactions, using oxygen can be facilitated by the addition of substances to the reaction medium which give rise to free radicals, for example, the ketone peroxides, hydrogen peroxide, tertiobutyl peroxide and azobisisobutyronitrile. If desired, the aforesaid substances may be added to the secondary alcohol for example, at a level of about 0.01 to 2% by weight.

The reaction can be carried out batch-wise or a continuous level of transformation can be employed, however, such is generally uneconomical. Similarly, while it is possible to reach the upper limit of transformation indicated above, it is known in this case that the selectivity of the reaction for the formation of peroxides is diminished and that there is a risk of attaining concentration of peroxides presenting the dangers of an explosion. The optimum level for the transformation should be selected bearing in mind the type of alcohol or alcohols employed and the operating conditions, factors which determine the stability of the peroxidic compounds.

While the peroxidic products can be concentrated by suitable means, as by removing the unreacted alcohol, it is advantageous for reasons of economy and safety to utilize the mixture resulting from the oxidation of secondary alcohol as is in the following step of oxidizing with ammonia in the presence of a nitrile.

An advantageous manner of carrying out the second oxidizing step comprises mixing the crude product resulting from the first oxidizing step with ammonia and cyanogen or the nitrile (IV) and carrying out the reaction at a temperature between about 0° and 100° for a period of time which is sufficient to consume the greater part of the peroxidic oxygen present in the reaction medium.

The second oxidizing step can be carried out in the presence of water or a solvent in order to facilitate the homogenization of the mixture. The solvent can advantageously be an alkyl monoalcohol containing 1 to 4 carbon atoms, as for example, methanol, ethanol, n-propanol, isopropanol, n-butanol, sec-butanol, isobutanol and tert-butanol.

The quantity of ammonia employed can advantageously be between about 0.2 and 5 moles per equivalent of peroxidic oxygen. The nitrile can be employed at a level of from about 1 to 10 moles per equivalent of peroxidic oxygen. If desired, one can add a quantity of ketone in the form of the peroxide corresponding to the starting alcohol to the reaction medium to add to the quantity of ketone contained therein. This additional quantity of ketone can be added at a level of from 1 to 2 moles per equivalent of peroxidic oxygen.

The ammonia utilized can be anhydrous or in aqueous solution. In the case of the latter, it is advantageous to employ a 15% concentration of $NH_3$ by weight.

It is advantageous to add from about 0.01 to 1% by weight of an agent to the mixture of the epoxidic products which will stabilize the peroxides and hydrogen peroxide, as for example, phosphoric acid, nitrilotriacetic acid, ethylenediaminetetraacetic acid and the sodium salts of the aforesaid acids. It is also advantageous to add a catalyst such as an ammonium or alkaline metal salt, especially a lithium, sodium or potassium salt of a hydracid, mineral oxyacid, aromatic or aliphatic carboxylic acid or alkyl or arylsulfonic acid containing less than about 20 carbon atoms, and wherein the anions are stable under the oxidizing conditions of the reaction medium. Examples of such catalysts include the ammonium or alkaline metal whose anions are: fluoride, chloride, sulfate, nitrate, phosphate, pyrophosphate, borate, carbonate, formate, acetate, propionate, butyrate, isobutyrate, hexanoate, octanoate, dodecanoate, stearate, oxalate, succinate, glutarate, adipate, benzoate, phthalate, methanesulfonate, ethanesulfonate, benzene sulfonate, p-toluenesulfonate and so forth. These salts can be employed as is or in the case of the ammonium salts, the salt can be generated in situ by addition of the appropriate acid to the reaction medium containing ammonia. The quantity of salt employed is advantageously from about 0.01 to 2% by weight of the total reaction medium.

The reaction of azine (II), urea, water and sulfuric acid is carried out at a temperature between about 50° and 150° C for a period ranging from about 2 to 7 hours in such a way that substantially all the ketone or aldehyde which is produced as a result of the reaction is recovered by distillation at atmospheric or reduced pressure.

The reactants can be combined in any order desired or simultaneously and at a rate permitting control of the heat of the reaction. It is also possible to pre-mix the water, urea and azine (II), raise the temperature of the solution to the desired level and then add the sulfuric acid. In a similar manner, the azine, sulfuric acid and water can be reacted first and the solution then heated to the necessary temperature during the course of the reaction.

The reactants can be employed in equimolar quantities or an excess of one or several of the reactants can be utilized. From about 2 to 10 moles of urea per mole of azine can be used, and advantageously, from about 2 to 4 moles of urea per mole of azine are reacted.

Water is employed at a ratio of from about 2 to 10 moles per mole of azine and the sulfuric acid can be used at a ratio of from about 1 to 10 moles per mole of azine. The urea can be in aqueous solution or in crystalline form. The sulfuric acid can be used in the form of a 20 to 40% aqueous solution.

The hydrazodicarbonamide prepared by the method of this invention precipitates as a white crystalline solid at a rate which is proportionate to the rate of the reaction. When the reaction has terminated, the degree of precipitation can be improved by the addition of water.

The hydrazodicarbonamide is an intermediate useful in a number of important syntheses, notably, for the manufacture of azodicarbonamide the use of which as a porophore agent is well known.

The following examples are illustrative of the method of this invention.

EXAMPLE 1

66 gm urea (1.1 moles), 19 gm water and 70 gm of 66° Be sulfuric acid were added to a glass reactor. The reaction medium was heated to 50° C providing a clear solution in to which were then progressively introduced 211 gm of an aqueous solution titrating 34.5% acetoneazine (0.65 moles), 10.4% methanol and 0.4% acetonitrile. Heating was continued until the temperature of the reaction medium reached 112° C. At the end of the addition of reactants, 26 gm of urea (0.43 moles) were added and the medium was left to react for an hour and a half at 112° C. Throughout the reaction, 64 gm of acetone (1.1 moles) liberated by the reaction were recovered by distillation. After cooling the medium to ambient temperature, 250 gm of water were added and the medium was then subjected to brisk agitation. The hydrazodicarbonamide precipitate was filtered, washed with water and dried. In this manner, 40 gm of hydrazodicarbonamide having a melting point of 244°-246° C corresponding to a yield of 52% by comparison to the amount of azine reacted were obtained.

EXAMPLE 2

112 gm of acetoneazine (1 mole) and 114 gm of water were placed in a glass reactor. 110 gm of 66° Be sulfuric acid, 100 gm of urea and 30 gm water were progressively added to the solution. The solution was heated to 110° C for 2 hours and the liberated acetone was distilled. In this manner 104 gm of acetone (1.8 moles) in aqueous solution were recovered. 30 gm of urea (0.5 moles) were then added to the reaction medium which was left to react for another hour. After cooling, the medium was diluted with 500 cm³ of water. The white precipitate was filtered and washed with water. 85.5 gm of hydrazodicarbonamide having a melting point of 244° C corresponding to a yield of 72.5% by comparison to the amount of azine reacted were obtained.

EXAMPLE 3

Example 1 was repeated replacing acetoneazine with 0.65 moles of methyethylketoneazine.

After a 2 hour reaction period, 42 gm of hydrazodicarbonamide having a melting point of 45° C, corresponding to a yield of 55% by comparison with the amount of azine reacted, were recovered.

EXAMPLE 4

Example 1 was repeated replacing acetoneazine with 91 gm isobutyraldazine (0.65 moles). 43 gm of hydrazodicarbonamide, corresponding to a yield of 56% by comparison with the azine reacted, were recovered.

We claim:

1. A method for preparing hydrazodicarbonamide

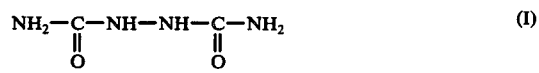

which comprises reacting at between about 50° and 150° C for a period of about 2–7 hours at atmospheric or subatmospheric pressure, urea, sulfuric acid, water and an azine of the formula

wherein $R_1$ is hydrogen or a $C_1$–$C_6$ alkyl, $R_2$ is a $C_1$–$C_6$ alkyl, and wherein said alkyl is straight or branched or a cycloalkyl, or $R_1$ and $R_2$ of both the $>C=N-$ moieties together form a straight or branched chain alkylene radical of from 3 to 5 carbon atoms, distilling off during the course of reaction substantially all the ketone or aldehyde formed, and recovering the hydrazodicarbonamide which forms from the reaction medium, wherein the amounts of reactants used per mol of azine are about 2–10 mols urea, about 2–10 mols of water and about 1–10 mols of sulfuric acid.

2. The method of claim 1 wherein from about 2 to 4 moles urea per mole of azine are employed.

3. A method for preparing hydrazodicarbonamide which comprises reacting at between about 50° and 150° C for a period of about 2–7 hours at atmosphere or subatmospheric pressure, acetoneazine and, per one mol of acetoneazine, about 2–10 mols urea, about 2–10 mols of water and about 1–10 mols of sulfuric acid, distilling off during the course of reaction substantially all the acetone formed, and recovering the hydrazodicarbonamide which forms from the reaction medium.

4. A method for preparing hydrazodicarbonamide

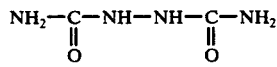   (I)

which comprises reacting at between about 50° and 150° C for a period of about 2–7 hours at atmospheric or subatmospheric pressure, urea, sulfuric acid, water and an azine of the formula

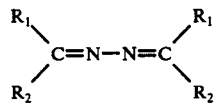   (II)

wherein $R_1$ is hydrogen or a $C_1$–$C_6$ alkyl, $R_2$ is a $C_1$–$C_6$ alkyl, and wherein said alkyl is straight or branched or a cycloalkyl, or $R_1$ and $R_2$ of both the $>C=N-$ moieties together form a straight or branched chain alkylene radical of from 3 to 5 carbon atoms, distilling off during the course of reaction substantially all the ketone or aldehyde formed, and recovering the hydrazodicarbonamide which forms from the reaction medium, wherein the amounts of reactants used per mol of azine are about 2–10 mols urea, about 2–10 mols of water and about 1–10 mols of sulfuric acid, said azine (II) being contained in a medium prepared by reacting in water or methanol or ethanol, isopropanol, n-butanol, sec-butanol, isobutanol or tert-butanol, about 0.2 to about 5 mols of a carbonyl compound of the general formula

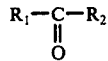   (III)

wherein $R_1$ and $R_2$ have the same meanings as in formula (II) with about 0.2 to about 5 mols of ammonia and 1 mol of hydrogen peroxide in the presence of from about 1 to about 10 equivalents, per mol of hydrogen peroxide, of cyanogen or acetonitrile, propionitrile, butyronitrile, isobutyronitrile, cyclohexyl nitrile, benzonitrile, tolunitriles, the cyanopyridines, the mono-, di- and trichloroacetonitriles, m-chlorobenzonitrile, p-methoxybenzonitrile, p-nitrogenzonitrile, m-trifluoromethyl benzonitrile, glycolonitrile, epsilonhydroxycapronitrile, cyanoacetic acid, the amide and $C_1$–$C_3$ alkyl esters of cyanoacetic acid, the amide and $C_1$–$C_3$ alkyl esters of beta-cyanopropionic acid, malonitrile, succinonitrile, glutaronitrile, adiponitrile, pimelonitrile, suberonitrile, the phthalonitriles, $\beta,\beta'$-oxydipropionitrile, $\beta$-methoxypropionitrile acrylonitrile, methacrylonitrile, or the cyanoethylation products of ethylene glycol, propylene glycol, glycerol and sorbitol.

5. A method for preparing hydrazodicarbonamide which comprises reacting at between about 50° and 150° C for a period of about 2–7 hours at atmospheric or subatmospheric pressure, acetoneazine and, per one mol of acetoneazine, about 2–10 mols urea, about 2–10 mols of water and about 1–10 mols of sulfuric acid, distilling off during the course of reaction substantially all the acetone formed, and recovering the hydrazodicarbonamide which forms from the reaction medium; said acetoneazine being contained in a medium prepared by reacting, in a mixture of water with at least one $C_1$–$C_4$ alkanol, hydrogen peroxide with, per mol of hydrogen peroxide, about 0.2 to 5 mols of acetone and about 0.2 to about 5 mols of ammonia in the presence of about 1 to about 10 mols of acetonitrile.

* * * * *

UNITED STATES PATENT AND TRADEMARK OFFICE
CERTIFICATE OF CORRECTION

PATENT NO. : 4,049,712
DATED : September 20, 1977
INVENTOR(S) : Jean-Pierre Schirmann and Francis Weiss It is certified that error appears in the above-identified patent and that said Letters Patent are hereby corrected as shown below:

Column 3, line 10, change "hexahydrobenaldehyde" to --hexahydrobenzaldehyde--

Column 3, line 10, change "p-nitrobenaldehyde" to --p-nitrobenzaldehyde--

Column 3, line 59, change "isobtuanol" to --isobutanol--

Column 7, line 58, change "Be" to --Be'--

Column 8, line 13, change "Be" to --Be'--

Signed and Sealed this

Twenty-eighth Day of March 1978

[SEAL]

Attest:

RUTH C. MASON
Attesting Officer

LUTRELLE F. PARKER
Acting Commissioner of Patents and Trademarks